(12) United States Patent
Ben-Sasson

(10) Patent No.: US 7,838,513 B2
(45) Date of Patent: Nov. 23, 2010

(54) ANTI-CANCER THERAPY COMPRISING AN H2-BLOCKER, AT LEAST ONE ANTIINFLAMMATORY AGENT AND A CYTOTOXIC AGENT

(75) Inventor: Shmuel A. Ben-Sasson, Jerusalem (IL)

(73) Assignee: Tiltan Pharma Ltd., Jerusalem (IL)

( * ) Notice: Subject to any disclaimer, the term of this patent is extended or adjusted under 35 U.S.C. 154(b) by 0 days.

(21) Appl. No.: 12/307,617

(22) PCT Filed: Jul. 4, 2007

(86) PCT No.: PCT/IL2007/000836

§ 371 (c)(1),
(2), (4) Date: Jan. 6, 2009

(87) PCT Pub. No.: WO2008/004231

PCT Pub. Date: Jan. 10, 2008

(65) Prior Publication Data

US 2009/0318391 A1 Dec. 24, 2009

Related U.S. Application Data

(60) Provisional application No. 60/819,164, filed on Jul. 7, 2006, provisional application No. 60/880,107, filed on Jan. 12, 2007.

(51) Int. Cl.
| | |
|---|---|
| A61K 31/66 | (2006.01) |
| A61K 31/44 | (2006.01) |
| A61K 31/425 | (2006.01) |
| A61K 31/415 | (2006.01) |
| A61K 31/34 | (2006.01) |

(52) U.S. Cl. .......... 514/110; 514/291; 514/352; 514/368; 514/370; 514/400; 514/471

(58) Field of Classification Search .......... 514/110, 514/291, 352, 368, 370, 400, 471
See application file for complete search history.

(56) References Cited

U.S. PATENT DOCUMENTS

2003/0158118 A1 8/2003 Weidner

2005/0148521 A1 7/2005 Ben-Sasson et al.

FOREIGN PATENT DOCUMENTS

| EP | 0584001 | * | 2/1994 |
|---|---|---|---|
| EP | 0584001 A1 | | 2/1994 |
| JP | 11228409 A | | 8/1999 |
| WO | 03/061566 A2 | | 7/2003 |
| WO | 2005/076987 A2 | | 8/2005 |
| WO | 2006/056889 A2 | | 6/2006 |
| WO | WO 2006/056889 | * | 6/2006 |

OTHER PUBLICATIONS

Sarloos, et al., Effects of histamine type-2 receptor antagonists on indomethacin and IL-2 immunotherapy of metastasis, Clin. Exp. Metastasis, 1993, vol. 11, 275-283.
Collins, et al., Histamine Receptor Antagonism and Anti-Tumour Activity, Br. J. Cancer, 1982, vol. 46, 817-820.
Natori, et al., Cimetidine inhibits angiogenesis and suppresses tumor growth, Biomedicine & Pharmacotherapy, 2005, vol. 59, 56-60.
Tetef, et al., Mitomycin C and menadione for the treatment of advanced gastrointestinal cancers: a phase II trial, J. Cancer Res Clin Oncol, 1995, vol. 121: 103-106.
Duffy, et al., Enhancement of Chemotherapeutic Drug Toxicity to Human Tumour Cells In Vitro by a Subset of Non-steroidal Anti-inflammatory Drugs (NSAIDs), European Journal of Cancer, 1998, vol. 34, No. 8, 1250-1259.
Saito, et al., All-trans Retinoic Acid Induces in Vitro Angiogenesis via Retinoic Acid Receptor: Possible Involvement of Paracrine Effects of Endogenous Vascular Endothelial Growth Factor Signaling, Endocrinology, 2007, vol. 148, No. 3, 1412-1423.
Powis, Free Radical Formation by Antitumor Quinones, Free Radical Biology & Medicine, 1989, vol. 6, 63-101.
DeVita, et al., Cancer: Principles and Practice of Oncology, 5th Edition, 1171-1175.

* cited by examiner

Primary Examiner—Raymond J Henley, III
(74) Attorney, Agent, or Firm—Nixon Peabody LLP

(57) ABSTRACT

The present invention relates to the treatment of a mammal with a pharmaceutical composition comprising an H2-blocker, at least one anti-inflammatory agent, a cytotoxic agent and, optionally, levamisole, a retinoid, an NFkB inhibitor, a redox quinone, an agent that enhances the intracellular accumulation of NADH+H+, a poly-alcohol, an inhibitor of pro-angiogenic growth factor(s) and an MMP inhibitor, such pharmaceutical composition allowing for the enhanced therapy and/or prevention of neoplastic diseases and disorders.

26 Claims, 4 Drawing Sheets

ANTI-CANCER THERAPY COMPRISING AN H2-BLOCKER, AT LEAST ONE ANTIINFLAMMATORY AGENT AND A CYTOTOXIC AGENT

CROSS-REFERENCE TO RELATED APPLICATIONS

This application is a 35 U.S.C. §371 National Stage of International Application No. PCT/IL2007/000836 filed on Jul. 4, 2007, which designates the United States, and which claims the benefit under 35 U.S.C. §119 (e) of U.S. Provisional Application No. 60/819,164 filed on Jul. 7, 2006, and U.S. Provisional Application No. 60/880,107 filed on Jan. 12, 2007, the contents of which are incorporated by reference herein in its entirety.

TECHNICAL FIELD OF THE INVENTION

The present invention relates to the field of anti-cancer therapy and/or prevention.

BACKGROUND OF THE INVENTION

Cancer generally refers to one of a group of more than 100 diseases caused by the uncontrolled, abnormal growth of cells that can spread to adjoining tissues or other parts of the body. Cancer cells can form a solid tumor, in which the cancer cells are massed together, or exist, as dispersed cells, as in leukemia. Normal cells divide until maturation is attained and then only as necessary for replacement of damaged or dead cells. Cancer cells are often referred to as "malignant", because they divide endlessly, eventually crowding out nearby tissues and spreading to other parts of the body. The tendency of cancer cells to invade and spread from one organ to another or from one part of the body to another distinguishes them from benign tumor cells, which overgrow but do not spread to other organs or parts of the body. Malignant cancer cells eventually metastasize and spread to other parts of the body via the bloodstream or lymphatic system, where they can multiply and form new tumors. This sort of tumor progression makes cancer a deadly disease.

Although there have been great improvements in the diagnosis and treatment of cancer, many people die from cancer each year, and their deaths are typically due to metastases and cancers that are resistant to conventional therapies.

Most drug-mediated cancer therapies rely on poisons, called cytotoxic agents, selective for dividing cells. These drugs are effective because cancer cells generally divide more frequently than normal cells. However, such drugs almost inevitably do not kill all of the cancer cells in the patient. One reason is that cancer cells can acquire mutations that confer drug resistance. Another is that not all cancer cells divide more frequently than normal cells, and slowly-dividing cancer cells can be as, or even more, insensitive to such cytotoxic agents as normal cells. Some cancer cells divide slowly, because they reside in a poorly vascularized, solid tumor and are unable to meet the needs required for cell division. For example, cytotoxic agents such as cyclophosphamide have been used to treat cancer.

Although cancer chemotherapy has advanced dramatically in recent years, treating cancers with a single agent has had limited success. Firstly, any single agent may only target a subset of the total population of malignant cells present, leaving a subpopulation of cancerous cells to continue growing. Secondly, cells develop resistance upon prolonged exposure to a drug. Combination therapies, which employ two or more agents with differing mechanisms of action and differing toxicities, have been useful for circumventing drug resistance and increasing the target cell population, but have not proven effective in the treatment of all cancers. In addition, certain combinations of agents may be synergistic: their combined effect is larger than that predicted based on their individual activities. Thus, combining different agents can be a powerful strategy for treating cancer.

The most striking difference between malignant and healthy cells is the capacity of cancer cells for unrestricted proliferation. This difference is exploited by many cytotoxic agents, which typically disrupt cell proliferation by interfering with the synthesis or integrity of DNA. Examples of classes of cytotoxic agents which function in this manner include alkylating agents, such as cyclophosphamide, antimetabolites (e.g. purine and pyrimidine analogues), and platinum coordination complexes.

One problem with cytotoxic agents which function by disrupting cell division is that they do not discriminate between normal and malignant cells: any dividing cell is a potential target for their action. Thus, cell populations which normally exhibit high levels of proliferation (such as bone marrow) are affected, leading to the toxic side effects commonly associated with cancer treatments.

As a tumor grows, it requires blood supply and, consequently, growth of new vasculature. Angiogenesis is a process of tissue vascularization that involves the growth of new developing blood vessels into a tissue, and is also referred to as neo-vascularization. Blood vessels are the means by which oxygen and nutrients are supplied to living cells.

Inhibitors of pro-angiogenic growth factors are agents used to inhibit the signaling of known pro-angiogenic factors like VEGF or FGF. Currently, these agents by themselves failed to demonstrate sufficient efficacy in the treatment of cancer.

With only a few exceptions, no single drug or drug combination is curative for most cancers. Thus, new drugs or combinations that can delay the growth of life-threatening tumors and/or improve quality of life by further reducing tumor load are needed.

Natori at al. (*Biomedicine & Pharmacotherapy*, 59: 56-60 (2005)) showed that Cimetidine, an H2-blocker, has anti-angiogenic properties and therefore anti-cancer properties. On the other hand, U.S. Patent Application 20030158118 (by Weidner, Morten and Sloth) showed that Cimetidine by itself did not inhibit tumor growth to any significant amount (Example 4 therein). Additionally, Saarloos M N et al. (*Clin. Exp. Metastasis* 11: 275-83 (1993)) performed immunotherapy tests on metastasis by administration of indomethacin plus interleukin-2 (IL-2), and showed that the addition of an H2-blocker did not improve the therapeutic efficacy. On the other hand, U.S. Patent Application 20030158118 suggested a cancer treatment composed of Cimetidine and a cysteine derivative.

Levamisole is a synthetic phenylimidothiazole which has been known in the art as an antihelmitic agent. While several studies failed to demonstrate any beneficial effect of Levamisole, by itself or in combination with 5-FU, others found some benefit for Levamisole when combined with 5-FU (DeVita et al. *Cancer: Principles and Practice of Oncology*, $5^{th}$ Edition, pp 1171-5).

Quinones are known for their ability to induce oxidative stress through redox cycling, hereby referred to as "Redox quinones" (Powis G., *Free Radic. Biol. Med.* 6:63-101 (1989)). Pharmaceutically acceptable redox quinones such as Vitamin $K_3$ have special therapeutic value since they are required for the bioactivation of proteins involved in hemostasis. Vitamin $K_3$ is a redox quinone, known as a prothrombogenic agent, mainly in supplement of veterinary diet. Studies have shown that Vitamin $K_3$ has failed to demonstrate beneficial anti-cancer properties (Tetef M. et al. *J. Cancer Res. Clin. Oncol.* 121:103-6 (1995)).

Retinoids are a class of chemical compounds that are related chemically to vitamin A. Retinoids are used in medicine, primarily due to the way they regulate epithelial cell growth. A natural retinoid, all-trans retinoic acid (ATRA), regulates a variety of important cellular functions via the retinoic acid receptor (RAR). ATRA has therapeutically been used against various malignancies including acute promyelocytic leukemia. Anti-tumor effects of retinoids are attributed to their influence on cell proliferation, differentiation, apoptosis and angiogenesis. However, there is still some uncertainty with respect to ATRA role in angiogenesis. For example, Saito A. et al. (*Endocrinology* 148:1412-23 (2007)) claimed that ATRA has a pro-angiogenic effect.

U.S. patent application No. US2005/148521 relates to methods and compositions for treating cancer comprising administering a combination of an effective amount of cytotoxic agent, a non steroidal anti inflammatory drug (NSAID), an ester of benzoic acid and a pharmaceutically acceptable carrier.

WO 06/056889 relates to methods and pharmaceutical compositions for inhibiting angiogenesis, comprising administering a combination of at least one angiogenesis inhibitor, at least one agent that enhances accumulation of intracellular NADH+H+ and a pharmaceutically acceptable carrier.

SUMMARY OF THE INVENTION

It has now surprisingly been found by the inventors of the present invention that a pharmaceutical composition comprising an H2-blocker (e.g. Cimetidine) with a cytotoxic agent and at least one anti-inflammatory drug (e.g. NSAID), augments the anti-tumor effect significantly when compared to the activity of each agent by itself.

Additionally, it has unexpectedly been found that further addition of an NFkB inhibitor (such as sulfasalazine) to a pharmaceutical composition comprising an H2-blocker, a cytotoxic agent, and at least one anti-inflammatory drug (e.g. NSAID) further enhances this anti-tumor effect.

Additionally, it has unexpectedly been found that further addition of a retinoid (such as all-trans retinoic acid (ATRA)) to a pharmaceutical composition comprising an H2-blocker, a cytotoxic agent, and at least one anti-inflammatory drug (e.g. NSAID) further enhances this anti-tumor effect.

Additionally, it has unexpectedly been found that addition of Levamisole to a pharmaceutical composition comprising an H2-blocker, a cytotoxic agent, and at least one anti-inflammatory drug (e.g. NSAID) promotes and enhances the anti-tumor activity of said drug combination.

Additionally, it has unexpectedly been found that addition of Levamisole to a pharmaceutical composition comprising an H2-blocker, a cytotoxic agent, at least one anti-inflammatory drug (e.g. NSAID) and an NFkB inhibitor promotes and enhances the anti-tumor activity of said drug combination.

Other agents, such as agents that enhance the intracellular accumulation of NADH+H+, inhibitors of a matrix metalloproteinase and inhibitors of pro-angiogenic factor(s) were also incorporated in the pharmaceutical compositions of the subject invention and unexpectedly showed an enhancement of anti-tumor effects.

The present invention thus provides a pharmaceutical composition comprising an H2-blocker, at least one anti-inflammatory agent, a cytotoxic agent and optionally, Levamisole, an NFkB inhibitor, a retinoid, a redox quinone, an agent that enhances the intracellular accumulation of NADH+H+, a poly-alcohol, an inhibitor of pro-angiogenic growth factor(s) and an MMP inhibitor and the use thereof for the treatment and/or prevention of cancer.

DETAILED DESCRIPTION OF THE INVENTION

Figure 1:
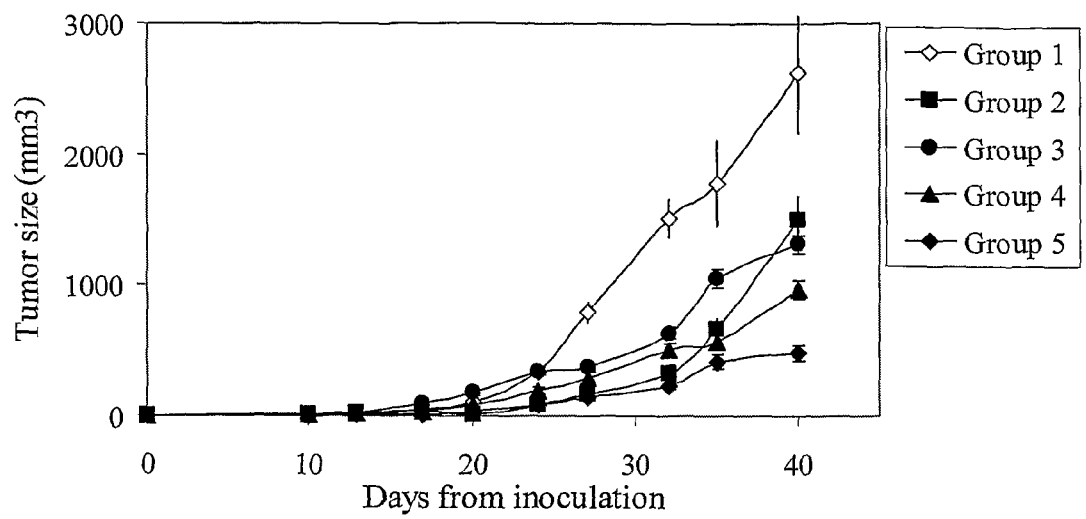
FIG. 1: Tumor size (in $mm^3$) after 40 days from tumor cell inoculation and administration of several pharmaceutical compositions of the present invention.

The present invention provides a pharmaceutical composition comprising: an H2-blocker, at least one anti-inflammatory agent, a cytotoxic agent and a pharmaceutically acceptable carrier.

The term "H2-blocker" as referred to in the present invention relates to an Histamine type 2-receptor antagonist, used to block the action of histamine on parietal cells in the stomach, decreasing acid production by these cells. The H2-blocker may be any H2-blocker known to those skilled in the art. For example, the H2-blocker may be selected from the group consisting of Cimetidine, Ranitidine, Famotidine and Nizatidine.

The term "anti-inflammatory agent (drug)" as used herein relates to any agents capable of reducing and/or inhibiting and/or preventing inflammation disease cased by either response to infection, injury, irritation, or surgery. In one embodiment of the invention, the anti-inflammatory agent may be selected from the group consisting of steroidal and non-steroidal anti-inflammatory agents. In another embodiment the anti-inflammatory drug is a steroidal anti-inflammatory drug selected from a group consisting of dexamethasone and betamethasone. In a further embodiment the anti-inflammatory agent is a non-steroidal anti inflammatory drug. In a specific embodiment the non-steroidal anti-inflammatory drug may be selected from a COX-1 inhibitor, a COX-2 inhibitor and a non-selective COX-1 and COX-2 inhibitor. In yet a further embodiment of the invention, the COX-1 and COX-2 inhibitors may be selected from the group consisting of diclofenac, piroxicam and indomethacin. In another embodiment, in addition to the non-steroidal anti-inflammatory drug, the composition further comprises a steroidal anti-inflammatory drug such as, but not limited to, dexamethasone and betamethasone.

The term "cytotoxic agent" as used herein relates to any agent used for the treatment of abnormal and uncontrolled progressive cellular growth. A cytotoxic agent acts as an angiogenesis inhibitor when administered at a low dose. Non limiting examples of cytotoxic agents include the alkylating agents cyclophosphamide (CTX) (Bristol-Meyers Squibb), ifosfamide (Bristol-Meyers Squibb), chlorambucil (Glaxo Wellcome), and carmustine (Bristol-Meyers Squibb); the anti-metabolites cytarabine (Pharmacia & Upjohn), 6-mercaptopurine (Glaxo Wellcome), 6-thioguanine (Glaxo Wellcome), and methotrexate (Immunex); the antibiotics doxorubicin (Pharmacia & Upjohn), daunorubicin (NeXstar), and mitoxantrone (Immunex); and miscellaneous agents such as vincristine (Lilly), vinblastine (Lilly), and paclitaxel (Bristol-Meyers Squibb). In one embodiment of the present invention, the cytotoxic agent may be selected from the group consisting of: cyclophosphamide, ifosfamide, cytarabine, 6-mercaptopurine, 6-thioguanine, vincristine, doxorubicin, daunorubicin, chlorambucil, carmustine, vinblastine, methotrexate, mitoxantrone, and paclitaxel or their pharmaceutically acceptable salts. In a further embodiment of the present invention, the cytotoxic agent may be cyclophosphamide or ifosfamide.

In the context of the present invention the term "pharmaceutically acceptable carrier" relates to pharmaceutically-acceptable, nontoxic carriers or diluents, which are defined as vehicles commonly used to formulate pharmaceutical compositions for animal or human administration. Such carriers may include, however not limited to, buffering agents, solubilizing agents, stabilizing agents or taste additives.

Each of the components of the pharmaceutical composition of the present invention, i.e. H2-blocker (e.g. cimetidine), cytotoxic agent (e.g. cyclophosphamide) and anti-inflammatory drug (e.g. NSAID), by itself did not demonstrate any significant anti-tumor effects. Example 2 (Group 3, FIG. 2) demonstrates that a single administration of cimetidine did not result in any significant effect on tumor growth. Additionally, Experiments 3 and 4 (FIGS. 3 and 4 respectively) in WO03/061566 demonstrated a very moderate effect of cyclophosphamide alone on tumor growth. Thus, it was surprisingly found that a pharmaceutical composition comprising an H2-blocker, a cytotoxic agent and an anti-inflammatory agent gave significant and enhanced anti-tumor effect.

In an embodiment of the present invention a pharmaceutical composition of the invention may further comprise Levamisole.

In a further embodiment of the present invention, a pharmaceutical composition of the invention also comprises an NFkB inhibitor.

The term "NFkB inhibitor" as used herein relates to any agent used for the inhibition of the Nuclear Factor kappa B (NFkB) intracellular transcription factor. In a specific embodiment, the NFkB inhibitor is selected from sulfasalazine, rapamycin, caffeic acid phenethylester, SN50 (a cell-permeable inhibitory peptide), parthenolide, triptolide, wedelolactone, lactacystin and MG-132 [Z-Leu-Leu-Leu-H]. In yet a further embodiment, the NFkB inhibitor is selected from sulfasalazine and rapamycin or their derivatives. In another embodiment rapamycin derivatives are selected from temsirolimus and everolimus.

In one embodiment of the invention, the pharmaceutical composition further comprises both Levamisol and an NFkB inhibitor together.

In a further embodiment of the present invention, a pharmaceutical composition of the invention also comprises a retinoid.

The term "retinoid" as used herein relates to a class of chemical compounds that are related chemically to vitamin A. As used herein, a retinoid component of the invention is any compound which acts through and/or binds to retinoic acid receptors (RARs) or to retinoid X receptors (RXRs). In a specific embodiment, the retinoid is an all trans retinoic acid (ATRA), known also as tretinoin or vesanoid (Roche Pharmaceuticals). ATRA can be isolated from natural sources or prepared synthetically.

In yet another embodiment of the present invention, a pharmaceutical composition of the invention may further comprise at least one agent that enhances intracellular accumulation of NADH+H$^+$. In a specific embodiment, the agent that enhances intracellular accumulation of NADH+H$^+$ is a poly-alcohol. In a further embodiment, the poly-alcohol is selected from the group consisting of xylitol, mannitol, sorbitol, arabinol, iditol and any other polyol known to those of skill in the art. In a specific embodiment, the poly-alcohol is xylitol.

In another embodiment of the present invention, a pharmaceutical composition of the invention may further comprise an inhibitor of a matrix metalloproteinase (MMP).

As used herein, the phrase "matrix metalloproteinase (MMP) inhibitor" relates to any chemical compound that inhibits by at least 5%, the hydrolytic activity of at least one matrix metalloproteinase enzyme that is naturally occurring in a mammal.

The MMP inhibitor may be any MMP inhibitor known in the art, such as AG-3340, RO 32-3555, RS 13-0830, Tissue Inhibitors of metalloproteinases (TIMPs) (e.g. TIMP-1, TIMP-2, TIMP-3, or TIMP-4), alpha 2-macroglobulin, tetracyclines (e.g., tetracycline, minocycline, and doxycycline), hydroxamates (e.g. batimastat, marimistat and trocade), chelators (e.g., EDTA, cysteine, acetylcysteine, D-penicillamine, and gold salts), synthetic MMP fragments, succinyl mercaptopurines, phosphonamidates, and hydroxaminic acids. In a specific embodiment, the MMP inhibitor is an MMP2 or an MMP9 inhibitor.

In another embodiment of the present invention, a pharmaceutical composition of the invention may further comprise an inhibitor of a pro-angiogenic growth factor.

The term "inhibitor of pro-angiogenic growth factor" relates to agents which are used to inhibit the signaling of known pro-angiogenic factors such as VEGF, FGF or PDGF. Without wishing to be bound by theory, it was shown that these agents can act extracellularly, by the inhibition of the interaction of an angiogenic factor with its receptor or can act intracellularly via the inhibition of the protein-kinase activity of the corresponding receptors. Non limiting examples of these agents include anti-VEGF or anti-VEGF-Receptor antibodies or inhibitors of the protein-kinase domain of VEGF-R, FGF-R or PDGF-R.

In another embodiment of the present invention, a pharmaceutical composition of the invention may further comprise a redox quinone.

Quinones are compounds having a fully conjugated cyclic dione structure, such as that of benzoquinones, derived from aromatic compounds by conversion of an even number of —CH= groups into —C(=O)— groups with any necessary rearrangement of double bonds (polycyclic and heterocyclic analogues are included). Quinones are known for their ability to induce oxidative stress through redox cycling, hereby referred to as "Redox quinones" (Powis G., *Free Radic. Biol Med.* 6:63-101 (1989)). Pharmaceutically acceptable redox quinones such as Vitamin K$_3$ have special therapeutic value since they are required for the bioactivation of proteins involved in hemostasis. Vitamin K$_3$ is a redox quinone, known as a prothrombogenic agent, mainly in supplement of veterinary diet. Studies have shown that Vitamin K$_3$ has failed to demonstrate beneficial anti-cancer properties (Tetef M. et al. *J. Cancer Res. Clin. Oncol.* 121:103-6 (1995)).

In one embodiment, the redox quinone is Vitamin $K_3$ (known as menadione or 2-methyl-1,4-naphthalenedione). In a further embodiment, Vitamin $K_3$ may be selected from a group consisting of menadione and menadione sodium-bisulfite.

A pharmaceutical composition of the invention as used herein relates to a combination of components/agents/compounds/drug/constituents.

Components/agents/compounds/drug/constituents as used herein are for example H2-blockers, anti-inflammatory agents, cytotoxic agents, levamisole, retinoids, NFkB inhibitors, agents that enhance the intracellular accumulation of $NADH+H+$, poly-alcohols, inhibitor of pro-angiogenic growth factor(s) or MMP inhibitors.

The term "container" as used herein refers to any receptacle capable of holding at least one component of a pharmaceutical composition of the invention. Such a container may be any jar, vial or box known to a person skilled in the art and may be made of any material suitable for the components contained therein and additionally suitable for short or long term storage under any kind of temperature.

The present invention further provides a formulation consisting of an aqueous or oily suspension or solution comprising a pharmaceutical composition of the invention.

In one embodiment, the formulation is formulated for oral administration. Such oral administration may allow for treatment to take place, for example, at the patient's home.

When a formulation of the subject invention comprises sulfasalazine, sulfasalazine may be dissolved using carbonate salts. Such a carbonate salt can be any carbonate salt such as sodium carbonate or sodium bicarbonate.

In a further embodiment of the present invention, the formulation further comprises a flavoring agent (e.g. menthol, anethol and/or salt). In another embodiment of the present invention, part of the constituents of the aqueous or oily suspension or solution of the formulation may be supplied in a dry form and reconstituted (e.g. solubilized) prior to oral administration.

In one embodiment of the present invention compositions may be provided as sustained release or timed release formulations. The carrier or diluent may include any sustained release material known in the art, such as glyceryl monostrearate or glyceryl distearate, alone or mixed with a wax. Micro-encapsulation may also be used. The timed release formulation can provide a pharmaceutical composition of immediate and pulsed release throughout the day. The diluent is selected so as not to affect the biological activity of a pharmaceutical composition of the invention. Examples of such diluents are distilled water, physiological saline, Ringer's solution, dextrose solution, and Hank's solution.

A pharmaceutical composition or formulation of the subject invention may include carriers, adjuvants and emulsifiers such as poloxamers, or nontoxic, non-therapeutic, non-immunogenic stabilizers and the like. Effective amounts of such diluent or carrier will be those amounts which are effective to obtain a pharmaceutically acceptable formulation in terms of solubility of components, biological activity, and the like.

In one embodiment, the formulations include a controlled-release device or composition where one or several of the components comprised in a pharmaceutical composition of the invention are being released in a delayed fashion. Such formulation may be in the form of a tablet (or a pill) which releases different doses of components comprised in a pharmaceutical composition of the invention, in different time intervals after being administered orally.

A pharmaceutical composition of the invention may be formulated in a solid, semi-solid, or liquid form such as, e.g. suspensions, aerosols, or the like or any other formulation known to a person skilled in the art. In one embodiment, the compositions are administered in unit dosage forms suitable for single administration of precise dosage amounts. The compositions may also include, depending on the formulation desired, pharmaceutically-acceptable carriers as defined above.

In one embodiment of the present invention, a pharmaceutical composition of the invention may be administered in a single dosage form comprising all the components together.

In another embodiment, at least one component of a pharmaceutical composition of the invention may be separately administered, simultaneously or sequentially.

In yet another embodiment, a pharmaceutical composition of the invention may be administered via a kit or a system comprising at least one component of a pharmaceutical composition of the invention in a separate container.

The term "administered sequentially" refers to ordered and successive administration of a pharmaceutical composition of the invention or their components comprised in separate containers. Said sequential administration may be 1, 2 or 3 days apart. Thus, the present invention further provides a kit comprising:
  a first container comprising at least one component of a pharmaceutical composition of the invention;
  a second container comprising at least one component of a pharmaceutical composition of the invention; and
  instructions for administration of said containers.

For example, instructions may indicate administration of a first container on non-consecutive days and for administration of a second container daily.

In a further embodiment, components of a pharmaceutical composition of the invention may be comprised in multiple, i.e. more than two, containers.

In one embodiment, the components of a pharmaceutical composition of the invention in the first and second container are the same. In another embodiment the components of a pharmaceutical composition of the subject invention in the first and second container are not the same. For ease of storage and administration, compatible components of a pharmaceutical composition of the invention may be placed in one container, separated from other components of said pharmaceutical composition.

According to one embodiment of the invention each component of a pharmaceutical composition of the invention, is contained in a separate container. In another embodiment, all components for administration on a particular day are combined and stored in one container for ease of use and storage. If necessary for stability purposes, the container may be stored frozen ($-20°$ C.) and thawed before administration, e.g., by placing in a refrigerator ($4-8°$ C.) one or two days before administration.

In one embodiment of the present invention, a kit comprises at least one vial of 1 0H2-blocker, at least one vial of an anti-inflammatory agent, at least one vial of a cytotoxic agent and, optionally, at least one vial of the following: levamisole, a retinoid, an NFkB inhibitor, an agent which increases intracellular accumulation of $NADH+H^+$, an inhibitor of a pro-angiogenic factor(s), an MMP inhibitor and a pharmaceutical carrier. The kit may contain instructions describing their use in administration which may be simultaneous or sequential.

Experiments conducted by the inventors of the present invention showed (Example 2 and FIG. 2) that neither the H2-blocker (cimetidine) alone, nor levamisole alone demonstrated any significant anti-cancer activity. However, it was surprisingly found by the inventors that the combination of cimetidine and levamisole with a cytotoxic agent, at least one anti-inflammatory agent and optionally at least one of an NFkB inhibitor, a retinoid, an agent that enhance the intracellular accumulation of NADH+H+, a poly-alcohol, an inhibitor of pro-angiogenic growth factor(s) and an MMP inhibitor resulted in an enhanced anti-tumor effect thereby yielding a powerful anti-cancer therapy.

Thus, the present invention provides a method of inhibiting cancer in a mammal comprising administering to the mammal a pharmaceutical composition of the invention.

The present invention further provides a method of inhibiting cancer in a mammal comprising administering to the mammal a formulation of the present invention.

The term "cancer" as referred to in the present invention relates to a neoplastic disease which is characterized by abnormal and uncontrolled cell division causing malignant growth or tumor. Cancer cells, unlike benign tumor cells, exhibit the properties of invasion and metastasis and are highly anaplastic. Cancer includes the two broad categories of carcinoma and sarcoma. In one embodiment of the present invention the cancer is a solid tumor or tumor metastasis. In a further embodiment of the present invention, said cancer may be selected from, however not limited to, the group consisting of lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, glioblastoma, benign tumor of the skin (e.g. keratoacanthomas), breast carcinoma (e.g. advanced breast cancer), kidney carcinoma, ovary carcinoma, bladder carcinoma and epidermal carcinoma.

The term "inhibiting cancer" as used in the context of the present invention relates to a decrease in tumor size; decrease in rate of tumor growth; stasis of tumor size; decrease in the number of metastasis; decrease in the number of additional metastasis; decrease in invasiveness of the cancer; decrease in the rate of progression of the tumor from one stage to the next, inhibition of tumor growth in a tissue of a mammal having a malignant cancer, control of establishment of metastases, inhibition of tumor metastases formation, regression of established tumors as well as decrease in the angiogenesis induced by the cancer. The term "inhibiting cancer" can also refer to prophylaxis such as prevention as cancer reoccurs after previous treatment (including surgical removal) and prevention of cancer in an individual prone (genetically, due to life style, chronic inflammation and so forth) to develop cancer.

The term "administering" or its other lingual forms as used in the context of the present invention relates to the path by which a pharmaceutically active component, a drug, fluid or other substance is brought into contact with the body. The pharmaceutical composition is transported from the site of entry to the part of the body where its action is desired to take place. According to one embodiment of the present invention, said administering may be achieved via any medically acceptable means suitable for a pharmaceutical composition of the invention or any component thereof, including oral, rectal, vaginal, nasal, topical, transdermal, or parenteral (including subcutaneous, intramuscular, intrasynovial, intraperitoneal, intradermal and intravenous) administration.

A pharmaceutical composition of the present invention or each component thereof can thus be administered by any means known in the art, such as oral (including buccal and sublingual), rectal, vaginal, nasal, topical, transdermal, or parenteral (including subcutaneous, intramuscular, intravenous, intrasynovial, intraperitoneal and intradermal) administration.

Pharmaceutical compositions, methods and systems of the present invention may be used either alone, or in conjunction with other cancer treatment methods known to those of skill in the art. Such methods may include, but are not limited to chemotherapy, radiation therapy or surgery. The administration of a pharmaceutical composition of the present invention may be conducted before, during or after other cancer therapies. In addition, a pharmaceutical composition of the present invention may be administered concurrently with other cancer treatments known to those of skill in the art.

Typically, oral administration requires a higher dose than intravenous administration. Thus, the administration route will depend upon the situation: the skilled artisan must determine which form of administration is best in a particular case, balancing dose needed versus the number of times per month administration is necessary.

In one embodiment the components of a pharmaceutical composition of the invention are administered using the normal dose of each component as known to a person skilled in the art.

In another embodiment the components of a pharmaceutical composition of the invention are administered using a lower dose than the dose known in the art, of one or more component. For example, when administering a cytotoxic agent, in order to reduce side effects, it is possible to use a lower dose than used when administered as a single cytotoxic agent-typically 75% or less of the individual amount, more specifically 50% or less, still more specifically 40% or less.

In particular, the agent that enhances intracellular accumulation of NADH+H$^+$ (i.e. polyol) is administered at a dose of 5 g to 100 g per day, more specifically at a dose of 10 g to 50 g per day.

Components comprised in a pharmaceutical composition of the present invention may be administered in dosages which may be found appropriate by a clinician, such as those described for individual components in the Physicians Desk Reference (PDR). Non limiting examples of suitable dosages of the components of a pharmaceutical composition of the invention include:

50 to 400 mg per day of levamisole, more specifically 100 to 300 mg per day of levamisole.

200 to 4,000 mg per day of cimetidine, more specifically, 400 to 2,000 mg per day of Cimetidine.

0.1-50 mg/kg of cyclophosphamide, more specifically 0.2-20 mg/kg of cyclophosphamide.

50 to 400 per day of diclofenac, more specifically, 100 to 300 mg per day of diclofenac.

50 to 5,000 mg per day of sulfasalazine, more specifically 300 to 3,000 mg per day of sulfasalazine.

1 to 10 mg per day, of rapamycin.

10 to 100 mg per day of all-trans-retinoic-acid (ATRA).

In one embodiment, a dosage of 0.1-50 mg/kg of cyclophosphamide, may be administered per day, twice a week or once a week. In a further embodiment, a dosage of 0.2-20 mg/kg of cyclophosphamide, may be administered per day, twice a week or once a week.

In therapeutic applications, the dosages and administration schedule of components of a pharmaceutical composition of the invention may vary depending on the component, the age, weight, and clinical condition of the recipient patient, and the experience and judgment of the clinician or practitioner administering the therapy, among other factors affecting the selected dosage. Generally, the dose and administration scheduled should be sufficient to result in slowing and/or regressing, the growth of the tumor(s) and may also cause complete regression of the cancer. In some cases, regression may be monitored via direct imaging (e.g. MRI) or by a decrease in blood levels of tumor specific markers. An effective amount of the pharmaceutical composition is that which provides a medical benefit as noted by the clinician or other qualified observer. Regression of a tumor in a patient is typically measured with reference to the diameter of a tumor. Decrease in the diameter of a tumor indicates regression. Complete regression is also indicated by failure of tumors to reoccur after treatment has stopped. The present invention allows for the administration of a pharmaceutical composition of the present invention, either prophylactically or therapeutically or in the context of adjuvant or neo-adjuvant treatment.

When provided prophylactically, a pharmaceutical composition of the invention may be administered in advance of any symptom. Prophylactic administration of pharmaceutical compositions may serve to prevent or inhibit cancer. A pharmaceutical composition of the invention may prophylactically be administered to a patient with, for example, a family history of cancer. The risk for developing cancer may be determined by measuring levels of cancer marker proteins in the biological fluids (i.e. blood, urine) of a patient or by genetic markers. Alternatively, administration of a pharmaceutical composition of the invention may be administered to a patient with rising cancer marker protein levels. Such markers include, for example, rising PSA, CEA, thymosin β-15, thymosin β-16, calcitonin, and matrix metalloproteinase (MMP). When provided prophylactically, the dose of a pharmaceutical composition of the invention may be reduced to the appropriate prophylactic dosage.

When provided therapeutically, a pharmaceutical composition of the invention may be administered at (or after) the onset of a symptom or indication of a cancer. Thus, a pharmaceutical composition of the present invention may be provided either prior to the anticipated tumor growth at a site or after the malignant growth has begun at a site.

The term "mammal" as used in the context of the present invention relates to warm blooded vertebrate animals characterized by the presence of mammary glands, which produce milk in females for the nourishment of young, and in addition are covered with hair or fur. In one embodiment, said mammal may be selected from the group consisting of a human, a cat, a dog and a horse.

The present invention further provides a system for the treatment or prevention of cancer comprising multiple containers, each container comprising at least one component of a pharmaceutical composition of the invention, to be administered on a scheduled day, the system comprising sufficient containers for at least one day of treatment. In another embodiment, the system may comprise sufficient containers for at least 7 days of treatment.

In a specific aspect of the present invention there is provided a system for treating cancer comprising:
   a first container comprising 25-100 ml aqueous solution of 0-60% xylitol comprising: cyclophosphamide in the range of 200-600 mg; diclofenac in the range of 100-300 mg; levamisole in the range of 0-200 mg; cimetidine in the range of 400-2,000 mg; sulfasalazine in the range of 100-1,000 mg or rapamycin in the range of 1-10 mg; and
   a second container comprising 25-100 ml aqueous solution of 0-60% xylitol comprising: cimetidine in the range of 400-2,000 mg; sulfasalazine in the range of 500-4,000 mg or rapamycin in the range of 1-10 mg; optionally levamisole in the range of 100-500 mg.

In another specific aspect of the present invention there is provided a system for treating cancer comprising:
   a first container comprising 25-100 ml aqueous solution of 0-60% xylitol comprising: cyclophosphamide in the range of 200-600 mg; diclofenac in the range of 100-300 mg; m cimetidine in the range of 200-2,000 mg; sulfasalazine in the range of 100-1,000 mg or rapamycin 1-10 mg; and
   a second container comprising 25-100 ml aqueous solution of 0-60% xylitol comprising: cimetidine in the range of 200-2,000 mg; sulfasalazine in the range of 300-4,000 mg or rapamycin 1-10 mg.

In yet another specific aspect of the present invention there is provided a system for treating cancer comprising:
   a first container comprising 25-100 ml aqueous solution of 0-60% xylitol comprising: cyclophosphamide in the range of 200-600 mg; diclofenac in the range of 100-300 mg; cimetidine in the range of 400-2,000 mg; ATRA in the range of 10-1.00 mg; and
   a second container comprising 25-100 ml aqueous solution of 0-60% xylitol comprising: cimetidine in the range of 400-2,000 mg; ATRA in the range of 10-100 mg.

In a further embodiment of the present invention there is provided a system having at least two vials for sequential administration. The system comprises:
   a first container (herein referred to as a "cytotoxic container") comprising at least one anti-inflammatory agent, a cytotoxic agent, an H2-blocker, optionally a poly-alcohol and a redox quinone, and a pharmaceutically acceptable carrier; and
   a separate second container (herein referred to as a "non cytotoxic container") comprising a H2-blocker and, optionally at least one of the following Levamisole, an NFkB inhibitor, a redox quinone, a retinoid, a poly-alcohol, an inhibitor of pro-angiogenic growth factor(s), a MMP inhibitor and a pharmaceutically acceptable carrier; the system may further comprise instructions for the administration of the components in the containers.

In yet a further aspect, the invention provides a system for treating cancer comprising:
   a container comprising at least one anti-inflammatory agent, a cytotoxic agent, and an H2-blocker, and optionally an NFkB inhibitor, a retinoid, a redox quinone, a poly-alcohol, and a pharmaceutically acceptable carrier; and
   a container comprising an H2-blocker and, optionally, Levamisole, an NFkB inhibitor, a retinoid, a redox quinone, a poly-alcohol, an inhibitor of pro-angiogenic growth factor(s), a MMP inhibitor and a pharmaceutically acceptable carrier.

A system of the present invention and it use in the treatment of cancer allows for a 7 day cycle of administration of at least one of the above components of a pharmaceutical composition of the invention. This cycle may include administration of at least one component of a pharmaceutical composition of the invention on non-consecutive days, while an agent that enhances intracellular accumulation of NADH+H+ may be administered daily during the rest of the 7 day cycle.

For instance, such a cycle may include twice a week administration of at least one component of a pharmaceutical composition of the invention on non-consecutive days while an agent that enhances intracellular accumulation of NADH+H+ may be administered daily during the rest of the 7 day cycle.

In one embodiment of the present invention, the system further comprises instructions to administer a first container on Days 1 and 4 of a 7 day cycle of treatment and administer a second container on Days 2, 3, 5, 6 and 7 of the cycle of treatment.

It is understood that the foregoing detailed description and the following examples are illustrative only and are not to be taken as limitations upon the scope of the invention. Various changes and modifications to the disclosed embodiments, which will be apparent to a person versed in the art, may be made without departing from the spirit and scope of the present invention. Further, all patents, patent applications, and publications cited herein are incorporated herein by reference.

In the following exemplary embodiments of the present invention, different pharmaceutical compositions of the invention were tested in vivo for the purpose of suppression of tumor growth in mice. The control group received a vehicle containing only non-active ingredients which was compared to groups which received pharmaceutical compositions comprising different active ingredients as described in detail below.

The following description depicts the experimental procedures preformed for the in vivo examples detailed herein below:

(a) Inoculation $3.5 \times 10^5$ cells of mouse mammary carcinoma (EMT$_6$/CTX) were injected subcutaneously in to 7-8 week-old mice of the CB6F1 strain (a cross between Balbc and C57bl), in the center of their backs. The mice were then marked and divided into groups. Typically, each group consisted of 7 to 8 mice.

(b) Tumor Measurement

The tumor size was measured twice a week and plotted in a graph. The formula used for assessing the 3 dimensional size of the tumor was: length×width×width×0.52. The width measurement was also used as an indication for tumor height, and the 0.52 is a normalizing factor.

(c) Injections

Mice were injected with a specified pharmaceutical composition, 6 days a week. Injection volume was 0.05 mL per 10 g body weight (25 g mice received 0.125 mL). All injections were performed intraperitoneally.

(d) Treatment Regimen

The week was divided into two treatment types, cytotoxic treatment and non-cytotoxic treatment days according to the corresponding composition.

Treatment was initiated once small tumors were visible on the majority of mice (approximately day 5 or 6 after inoculation). The first treatment was cytotoxic and marked as day 1 of the week (D1).

Cytotoxic treatment was administered on day 1 and 4 of each week (D1 and D4 respectively). Non-cytotoxic treatment was given on days 2, 3, 5 and 6 (D2, D3, D5 and D6 respectively). No treatment was given on the 7th day. The control group was administered the vehicle every day.

(e) Pharmaceutical Composition:

Non-cytotoxic treatment comprised the following: xylitol—60% and either cimetidine and/or levamisole and/or sulfasalazine and/or menadione (in Examples 2 and 3 only) and/or no active ingredient (=control), according to the experimental design described in the table of the corresponding example.

For the cytotoxic treatment, the following components were added to the previously described (non-cytotoxic) pharmaceutical composition: diclofenac sodium—30 mg/Kg/day, cyclophosphamide (CTX)—60 mg/Kg/day, according to the experimental composition described in the table of the corresponding example.

All components mentioned above were delivered in a vehicle containing Double Distilled Water (DDW), 2% Solutol HS-15 and 60% Xylitol. In experiments 1 and 7, the vehicle contained only DDW; no Xylitol was added.

The daily dosage of sulfasalazine was administered according to the experimental regimen, and ranges between 150-350 mg/Kg/day, according to the experimental design described in the table of the corresponding example.

For all non-sulfasalazine containing compositions: DDW volume added was 60% of final volume of solution due to xylitol dissolving and volume increase. 60% xylitol was dissolved in preheated DDW (~60° C.) and stirred until solution was clear. 98% of final solution volume was measured and 2% solutol (liquid) was added. All other components were then added to the xylitol solution and stirred until solution was homogenous.

For compositions containing sulfasalazine: DDW volume added was 60% of final volume of solution due to xylitol dissolving and volume increase. In order to increase sulfasalazine solubility, the pH of the solution was brought to basic ranges (pH~10.5). This was achieved by adding Na$_2$CO$_3$ to DDW to a concentration of 0.2M. sulfasalazine was then added and the pH neutralized. Solution was heated (~60° C.) and 60% xylitol added. 98% of final solution volume was measured and 2% solutol (liquid) was added. All other components were then added to the xylitol solution and stirred until solution was homogenous.

Example 1

Table 1 describes the pharmaceutical compositions administered to Groups 1 to 5:

TABLE 1

Pharmaceutical Compositions of Example 1

| Component & dosage | Group 1 (Control) | Group 2 | Group 3 | Group 4 | Group 5 |
|---|---|---|---|---|---|
| Vehicle | + | + | + | + | + |
| Cimetidine 20 mg/Kg all week | | + | | + | + |
| Sulfasalazine 150 mg/Kg on non-cytotoxic days, 50 mg/Kg on cytotoxic days | | | | | + |
| Diclofenac 30 mg/Kg on cytotoxic days | | + | + | + | + |
| CTX 60 mg/Kg on cytotoxic days | | | + | + | + |

This experiment was conducted in order to show the contribution of either cimetidine by itself or together with sulfasalazine to the anti-tumor activity when added to the combination of CTX and diclofenac. The results are depicted in FIG. 1. The pharmaceutical composition comprising cimetidine (Group 4) showed a more pronounced anti-tumor effect demonstrated by the reduction in tumor size, compared to the anti-tumor effect of the pharmaceutical compositions comprising only CTX and diclofenac (Group 3) or a composition comprising diclofenac, sulfasalazine and cymetidine (Group 2). The addition of both cimetidine and sulfasalazine to the pharmaceutical composition (Group 5), gave the most pronounced reduction in tumor size.

Example 2

Table 2 describes the pharmaceutical compositions administered to Groups 1 to 4.

TABLE 2

Pharmaceutical Compositions of Example 2

| Component & dosage | Group |  |  |  |
| --- | --- | --- | --- | --- |
|  | Group 1 (Control) | Group 2 | Group 3 | Group 4 |
| Vehicle | + | + | + | + |
| Levamisole 12 mg/Kg on non-cytotoxic days |  | + |  | + |
| Cimetidine 20 mg/Kg all week |  |  | + | + |

Figure 2:
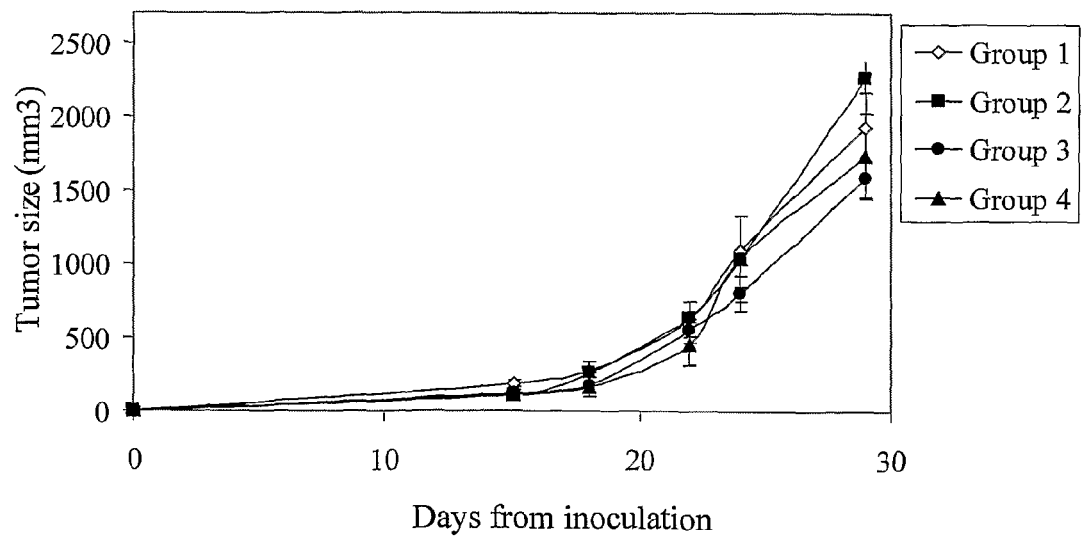
FIG. 2: Tumor size (in $mm^3$) after 28 days from tumor cell inoculation and administration of cimetidine and/or levamisole.

The results as depicted in FIG. 2, show that neither levamisole (Group 2), nor cimetidine (Group 3), nor their combination (Group 4) had any significant effect on tumor growth.

Example 3

Table 3 descries the pharmaceutical compositions administered to Groups 1 to 3:

TABLE 3

Pharmaceutical Compositions of Example 3.

| Component & dosage | Group |  |  |
| --- | --- | --- | --- |
|  | Group 1 (Control) | Group 2 | Group 3 |
| Vehicle | + | + | + |
| Levamisole 12 mg/Kg on non-cytotoxic days |  |  | + |
| Cimetidine 20 mg/Kg all week |  |  | + |
| Menadione 27.5 mg/Kg all week |  | + | + |
| Sulfasalazine 150 mg/Kg on non-cytotoxic days, 50 mg/Kg on cytotoxic days |  | + | + |
| Diclofenac 30 mg/Kg on cytotoxic days |  | + | + |
| CTX 60 mg/Kg on cytotoxic days |  | + | + |

Figure 3:
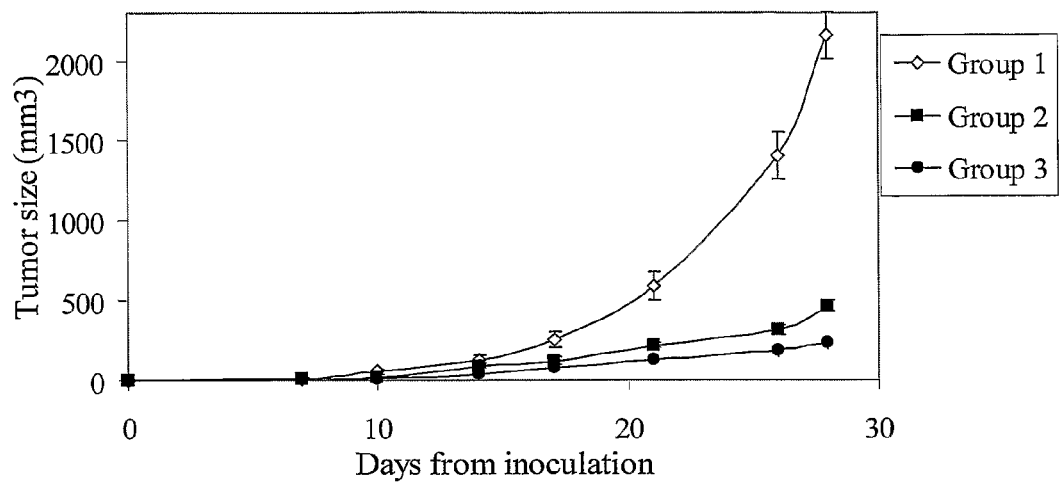
FIG. 3: Tumor size (in $mm^3$) after 28 days from tumor cell inoculation and administration of several pharmaceutical compositions of the present invention.

FIG. 3 shows a significant reduction in tumor size upon the addition of cimetidine and levamisole to pharmaceutical compositions comprising combinations of CTX, diclofenac, sulfasalazine and menadione (Group 3 vs. Group 2, in FIG. 3) (as compared to control group). A significant reduction in tumor size was observed for Group 2 and Group 3. Hence, the concomitant addition of cimetidine and levamisole enhanced the anti-tumor activity of pharmaceutical compositions comprising combinations of CTX, diclofenac, sulfasalazine and menadione.

Example 4

Table 4 describes the pharmaceutical compositions administered to Groups 1 to 3:

TABLE 4

Pharmaceutical Compositions of Example 4

| Component & dosage | Group |  |  |
| --- | --- | --- | --- |
|  | Group 1 (Control) | Group 2 | Group 3 |
| Vehicle | + | + | + |
| Levamisole 12 mg/Kg on non-cytotoxic days |  |  | + |
| Cimetidine 20 mg/Kg all week |  |  | + |
| Menadione 27.5 mg/Kg all week |  | + | + |
| Diclofenac 30 mg/Kg on cytotoxic days |  | + | + |
| CTX 60 mg/Kg on cytotoxic days |  | + | + |

Figure 4:
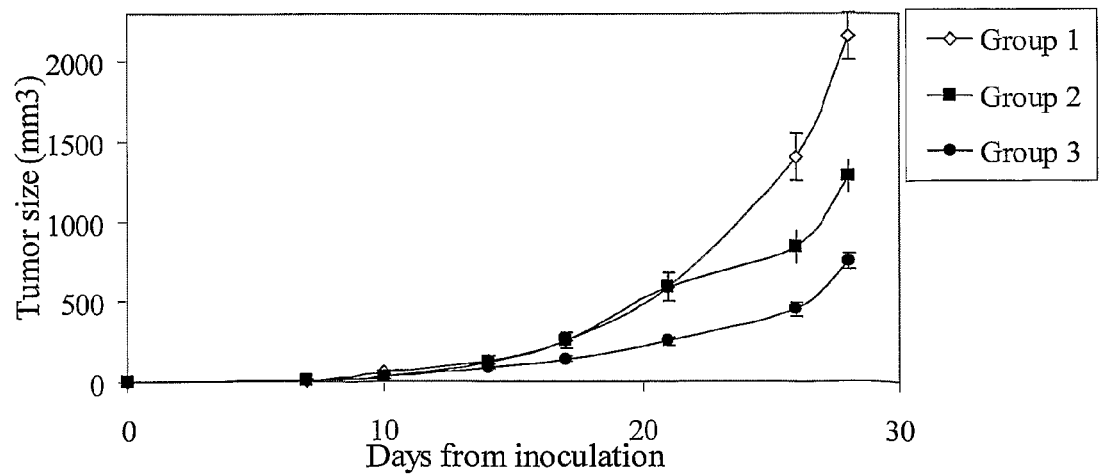
FIG. 4: Tumor size (in $mm^3$) after 28 days from tumor cell inoculation and administration of several pharmaceutical compositions of the present invention.

The pharmaceutical compositions of this experiment are similar to the compositions of Experiment 2, with the absence of sulfasalazine in the combination of either cytotoxic or non-cytotoxic treatments. The results are depicted in FIG. 4. Reduction in tumor size was achieved upon addition of cimetidine and levamisole to pharmaceutical compositions comprising combinations of CTX, diclofenac and menadione (as compared to control group).

Example 5

Table 5 describes the pharmaceutical compositions administered to Groups 1 to 4:

TABLE 5

Pharmaceutical Compositions of Example 5

| Component & dosage | Group |  |  |  |
| --- | --- | --- | --- | --- |
|  | Group 1 (Control) | Group 2 | Group 3 | Group 4 |
| Vehicle | + | + | + | + |
| Levamisole 12 mg/Kg on non-cytotoxic days |  |  | + | + |
| Cimetidine 20 mg/Kg all week |  | + |  | + |
| Diclofenac 30 mg/Kg on cytotoxic days |  | + | + | + |
| CTX 60 mg/Kg on cytotoxic days |  | + | + | + |

Figure 5:
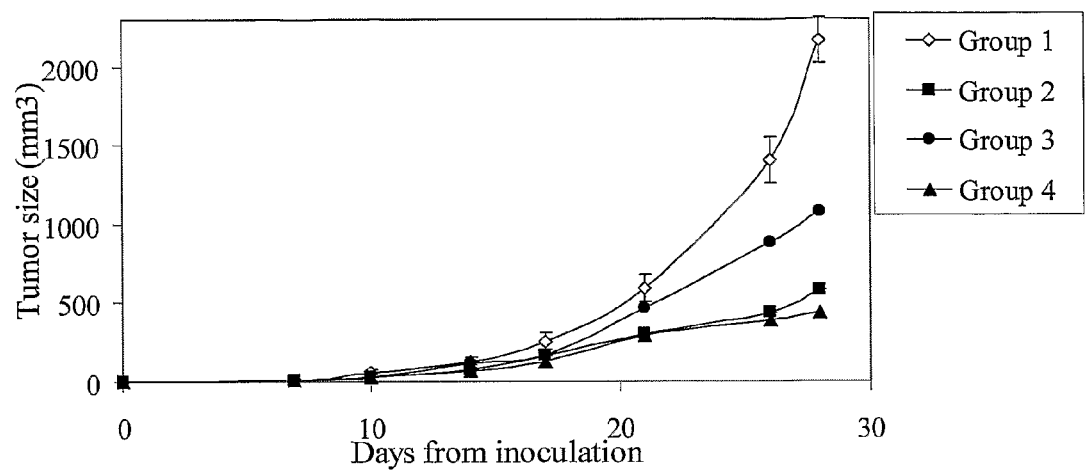
FIG. 5: Tumor size (in $mm^3$) after 28 days from tumor cell inoculation and administration of several pharmaceutical compositions of the present invention.

This experiment was conducted in order to show the contribution of either cimetidine or levamisole or their combination to the anti-tumor activity when added to CTX and diclofenac. The results are depicted in FIG. 5. The pharmaceutical composition comprising cimetidine (Group 2) showed a more pronounced anti-tumor effect reducing the tumor size, compared to pharmaceutical compositions comprising levamisole (Group 3). The addition of both cimetidine and levamisole to the pharmaceutical composition (Group 4), gave the most pronounced tumor size reduction.

Example 6

Table 6 describes the pharmaceutical compositions administered to Groups 1 to 4:

TABLE 6

Pharmaceutical Compositions of Example 6

| Component & dosage | Group 1 (Control) | Group 2 | Group 3 | Group 4 |
|---|---|---|---|---|
| Vehicle | + | + | + | + |
| Levamisole 12 mg/Kg on non-cytotoxic days | | | | + |
| Cimetidine 20 mg/Kg all week | | | + | + |
| Sulfasalazine 150 mg/Kg on non-cytotoxic days, 50 mg/Kg on cytotoxic days | | + | + | + |
| Diclofenac 30 mg/Kg on cytotoxic days | | + | + | + |
| CTX 60 mg/Kg on cytotoxic days | | + | + | + |

Figure 6:
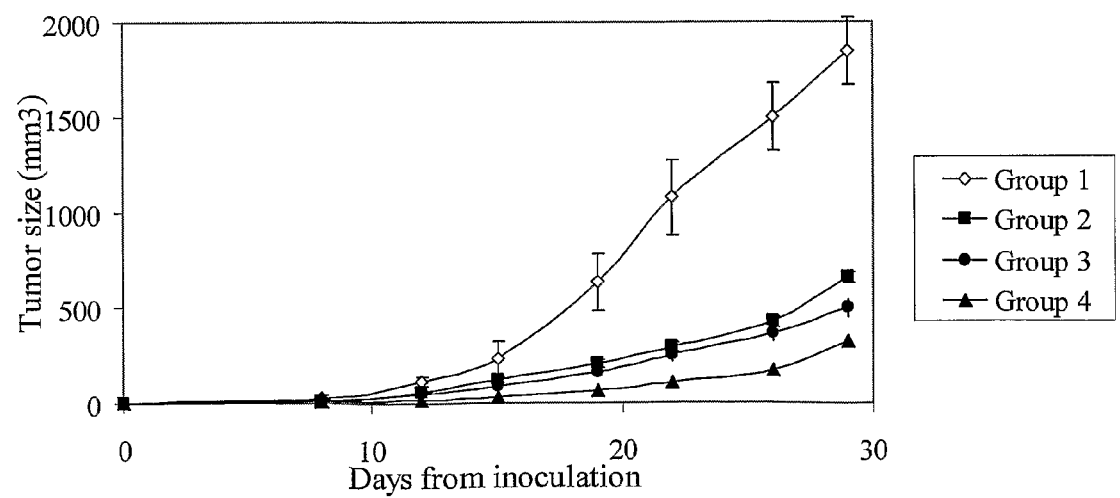
FIG. 6: Tumor size (in $mm^3$) after 28 days from tumor cell inoculation and administration of several pharmaceutical compositions of the present invention.

This experiment was conducted in order to show the contribution of either cimetidine by itself or together with levamisole to the anti-tumor activity when added to the combination of CTX, diclofenac and sulfasalazine. The results are depicted in FIG. 6. The pharmaceutical composition comprising cimetidine (Group 3) showed significantly more pronounced anti-tumor effect reducing the tumor size, compared to the same pharmaceutical compositions but without cimetidine (Group 2). The addition of both cimetidine and levamisole to the pharmaceutical composition (Group 4), gave the most pronounced reduction in tumor size.

Example 7

Table 7 describes the pharmaceutical compositions administered to Groups 1 to 4:

TABLE 7

Pharmaceutical Compositions of Example 7

| Component & dosage | Group 1 (Control) | Group 2 | Group 3 | Group 4 |
|---|---|---|---|---|
| Vehicle | + | + | + | + |
| All Trans Retinoic acid (ATRA) 30 mg/Kg on non-cytotoxic days, 60 mg/Kg on cytotoxic days | | | | + |
| Cimetidine 20 mg/Kg all week | | | + | + |
| Sulfasalazine 150 mg/Kg on non-cytotoxic days, 50 mg/Kg on cytotoxic days | | | + | |
| Diclofenac 30 mg/Kg on cytotoxic days | | + | + | + |
| CTX 60 mg/Kg on cytotoxic days | | + | + | + |

Figure 7:
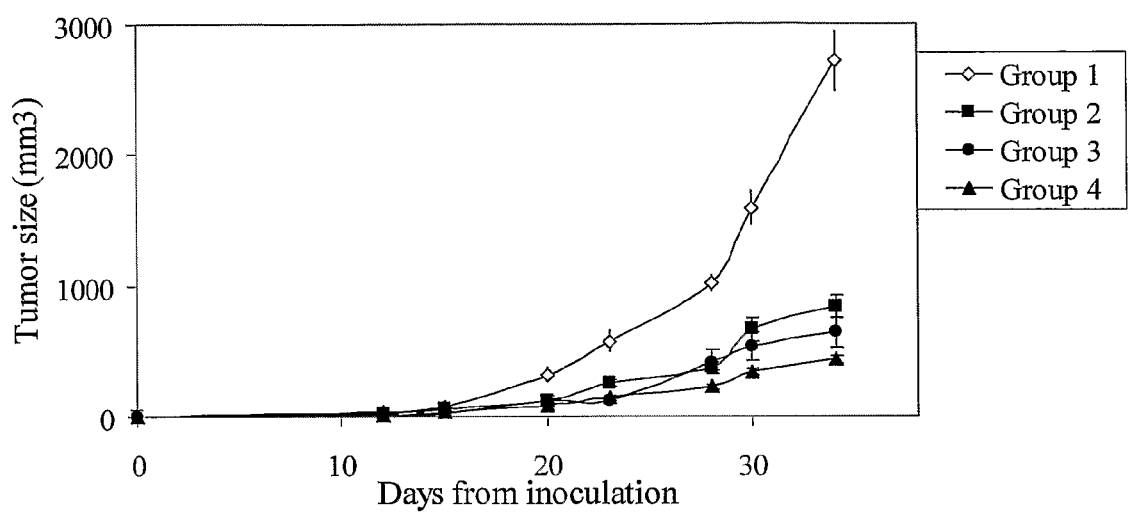
FIG. 7: Tumor size (in $mm^3$) after 35 days from tumor cell inoculation and administration of several pharmaceutical compositions of the present invention.

This experiment was conducted in order to show the contribution of either sulfasalazine or All Trans Retinoic Acid (ATRA) to the anti-tumor activity when added to the combination of CTX, diclofenac and cimetidine. The results are depicted in FIG. 7. The pharmaceutical composition comprising cimetidine and sulfasalazine (Group 3) showed more pronounced anti-tumor effect reducing the tumor size, compared to pharmaceutical compositions comprising CTX and diclofenac (Group 2). While the replacement of sulfasalazine by ATRA (Group 4), gave the most pronounced reduction in tumor size.

Example 8

(a) Tested Subject

A female breast cancer patient with metastases at bone, lung, liver and neck, was enrolled into treatment with a pharmaceutical composition of the invention. Treatment was commenced after unsatisfactory results with other hormone therapy treatments and also other state-of-the-art chemotherapy treatment comprising Vinorelbine and Capcitabine. Two months prior to treatment with the composition, the tumor size increased by 25%.

(b) Monitoring

Progression of disease was monitored every 6-8 weeks by a CT measurement of patient's tumor size.

(c) Pharmaceutical Composition and Administration Thereof

The product was packed in 2 types of individual color-coded vials:

Blue capped vials containing cyclophosphamide, cimetidine., sulfasalazine and diclofenac sodium in the amounts specified in the Table 8 below.

Red capped vials containing sulfasalazine and cimetidine, in the amounts specified in Table 8 below.

Weekly doses were packed in kits (Styrofoam containers) that include 7 vials corresponding to a daily dose, and labeled according to the administration day: Two blue capped vials (days 1 and 4), and five red capped vials (days 2, 3, 5, 6 and 7).

The therapeutic product was supplied in 3 set doses: 25 ml, 37.5 ml, and 50 ml. The patient received the 25 ml vials during the 1st week of treatment, the 37.5 ml vials during the 2nd week, and from the 3rd week and on, she received the full dose of 50 ml.

The weekly treatment cycle began on Sunday. The Blue capped vials were administered orally on Sunday and Wednesday while the Red capped vials were administered on Monday, Tuesday, Thursday, Friday and Saturday.

TABLE 8

Pharmaceutical Composition of Example 8

| Component | 25 ml vials | 37.5 ml vials | 50 ml vials |
|---|---|---|---|
| Blue Capped Vials | | | |
| Cyclophosphamide | 200 mg | 300 mg | 400 mg |
| Cimetidine | 200 mg | 300 mg | 400 mg |
| Sulfasalazine | 150 mg | 225 mg | 300 mg |
| Diclofenac Sodium | 100 mg | 150 mg | 200 mg |
| Red Capped Vials | | | |
| Sulfasalazine | 450 mg | 675 mg | 900 mg |
| Cimetidine | 200 mg | 300 mg | 400 mg |

(d) Results

After 3 months of treatment, there was no noted progression of the disease (i.e. 0% change in tumor-size), while after 5 months with the above treatment, the tumor grew only by 1% (as opposed to 25% during 2 months prior to treatment). These results demonstrate that the treatment according to the present invention causes a dramatic decrease in tumor growth.

The invention claimed is:

1. A pharmaceutical composition comprising: an H2-blocker, at least one non-steroidal anti-inflammatory agent, a cytotoxic agent and a pharmaceutically acceptable carrier.

2. The pharmaceutical composition of claim 1, wherein the composition further comprises levamisol.

3. The pharmaceutical composition of claim 1, wherein the composition further comprises an NFkB inhibitor.

4. The pharmaceutical composition of claim 1, wherein the composition further comprises at least one agent that enhances intracellular accumulation of $NADH+H^+$.

5. The pharmaceutical composition of claim 1, wherein the composition further comprises an inhibitor of a matrix metalloproteinase.

6. The pharmaceutical composition of claim 1, wherein the composition further comprises an inhibitor of a pro-angiogenic factor.

7. The pharmaceutical composition of claim 1, wherein the composition further comprises a redox quinone.

8. The pharmaceutical composition of claim 7, wherein the redox quinone is Vitamin $K_3$.

9. The pharmaceutical composition of claim 8, wherein Vitamin $K_3$ is selected from a group consisting of menadione and menadione sodiumbisulfite.

10. The pharmaceutical composition of claim 1, wherein the cytotoxic agent is selected from the group consisting of: cyclophosphamide, ifosfamide, cytarabine, 6-mercaptopurine, 6-thioguanine, vincristine, doxorubicin, daunorubicin, chlorambucil, carmustine, vinblastine, methotrexate, mitoxantrone, and paclitaxel or their pharmaceutically acceptable salts.

11. The pharmaceutical composition of claim 10, wherein the cytotoxic agent is cyclophosphamide or ifosfamide.

12. The pharmaceutical composition of claim 1, wherein the non-steroidal anti-inflammatory agent is selected from a group consisting of COX-1 and COX-2 inhibitors.

13. The pharmaceutical composition of claim 12, wherein the non-steroidal anti-inflammatory agent is selected from the group consisting of diclofenac, piroxicam and indomethacin.

14. The pharmaceutical composition of claim 4, wherein the agent that enhances intracellular accumulation of $NADH+H^+$ is a poly-alcohol.

15. The pharmaceutical composition of claim 14, wherein the poly-alcohol is selected from the group consisting of xylitol, mannitol, sorbitol, arabinol, and iditol.

16. The pharmaceutical composition of claim 15, wherein the poly-alcohol is xylitol.

17. The pharmaceutical composition of claim 1, wherein the H2-blocker is selected from the group consisting of cimetidine, ranitidine, famotidine and nizatidine.

18. The pharmaceutical composition of claim 1 wherein the composition further comprises a retinoid.

19. The pharmaceutical composition of claim 18, wherein the retinoid is all-trans-retinoic-acid (ATRA).

20. The pharmaceutical composition of claim 3 wherein the NFkB inhibitor is sulfasalazine or rapamycin.

21. A formulation consisting of an oily suspension or an aqueous suspension or solution comprising the pharmaceutical composition of claim 1.

22. A formulation of claim 21 for oral administration.

23. A kit comprising:
   a first container comprising a composition comprising at least one anti-inflammatory agent, a cytotoxic agent, an H2-blocker, optionally an NFkB inhibitor, a retinoid, a redox quinine, a poly-alcohol, and a pharmaceutically acceptable carrier;

a second container comprising a composition comprising an H2-blocker and, optionally, Levamisole, an NFkB inhibitor, a retinoid, a redox quinine, a poly-alcohol, an inhibitor of pro-angiogenic growth factor(s), a MMP inhibitor and a pharmaceutically acceptable carrier; and instructions for administration.

24. A method of inhibiting cancer in a mammal comprising administering to the mammal a pharmaceutical composition of claim 1, wherein said cancer is selected from the group consisting of lung cancer, pancreatic cancers, colon cancers, prostate cancer, hematopoietic tumors of lymphoid lineage, myeloid leukemias, thyroid follicular cancer, myelodysplastic syndrome, tumors of mesenchymal origin, melanomas, teratocarcinomas, neuroblastomas, gliomas, glioblastoma, benign tumor of the skin, breast carcinoma, kidney carcinoma, ovary carcinoma, bladder carcinoma and epidermal carcinoma.

25. A method of inhibiting cancer in a mammal comprising administering to the mammal a formulation of claim 21, wherein said cancer is selected from the group consisting of lung cancer, pancreatic cancers, colon cancers, prostate cancer, hematopoietic tumors of lymphoid lineage, myeloid leukemias, thyroid follicular cancer, myelodysplastic syndrome, tumors of mesenchymal origin, melanomas, teratocarcinomas, neuroblastomas, gliomas, glioblastoma, benign tumor of the skin, breast carcinoma, kidney carcinoma, ovary carcinoma, bladder carcinoma and epidermal carcinoma.

26. A system for treating cancer comprising:
  a container comprising at least one anti-inflammatory agent, a cytotoxic agent, an H2-blocker, optionally an NFkB inhibitor, a retinoid, a redox quinine, a poly-alcohol, and a pharmaceutically acceptable carrier; and
  a container comprising an H2-blocker and, optionally, Levamisole, an NFkB inhibitor, a retinoid, a redox quinone, a poly-alcohol, an inhibitor of pro-angiogenic growth factor(s), a MMP inhibitor and a pharmaceutically acceptable carrier,
wherein said cancer is selected from the group consisting of lung cancer, pancreatic cancers, colon cancers, prostate cancer, hematopoietic tumors of lymphoid lineage, myeloid leukemias, thyroid follicular cancer, myelodysplastic syndrome, tumors of mesenchymal origin, melanomas, teratocarcinomas, neuroblastomas, gliomas, glioblastoma, benign tumor of the skin, breast carcinoma, kidney carcinoma, ovary carcinoma, bladder carcinoma and epidermal carcinoma.

* * * * *